(12) United States Patent
Hof (10) Patent No.: US 8,172,572 B2
(45) Date of Patent: May 8, 2012

(54) DENTAL TOOL DISPLACEMENT APPARATUS WITH SLOW ROTATIONAL MOTION

(75) Inventor: Raphael Hof, Kfar Yona (IL)

(73) Assignee: Redent-Nova Ltd., Ra'anana (IL)

( * ) Notice: Subject to any disclaimer, the term of this patent is extended or adjusted under 35 U.S.C. 154(b) by 233 days.

(21) Appl. No.: 12/545,883

(22) Filed: Aug. 24, 2009

(65) Prior Publication Data
US 2010/0330528 A1    Dec. 30, 2010

Related U.S. Application Data

(60) Provisional application No. 61/219,812, filed on Jun. 24, 2009.

(51) Int. Cl.
*A61C 1/02* (2006.01)
*A61C 1/07* (2006.01)
(52) U.S. Cl. ........................................ 433/105; 433/122
(58) Field of Classification Search .................. 433/102, 433/105, 122, 123; 173/49, 109, 110
See application file for complete search history.

(56) References Cited

U.S. PATENT DOCUMENTS

| 4,479,516 A * | 10/1984 | Hunter ............................. 15/22.1 |
| 6,106,290 A * | 8/2000 | Weissman ....................... 433/122 |
| 2002/0025504 A1 * | 2/2002 | Satake et al. ................... 433/106 |

FOREIGN PATENT DOCUMENTS

IL    WO2005070320    8/2005

* cited by examiner

*Primary Examiner* — John J Wilson
(74) *Attorney, Agent, or Firm* — Mark M Friedman (57) ABSTRACT

A dental tool displacement apparatus for use with a motorized power handle to displace a dental tool includes a tool holder having a receptacle for receiving the dental tool, and a drive arrangement. The drive arrangement defines a transmission from the motorized power handle to the tool holder such that the tool holder undergoes reciprocating motion parallel to the tool axis at a first frequency of oscillations per minute and rotates about the tool axis at a second frequency of rotations per minute. In some cases, the two types of motion are generated by an eccentric drive pin engaging an annular slot which has gear teeth along one side, thereby generating an angular rotation step of the tool holder during each reciprocating stroke. In some cases, the first frequency is at least one order of magnitude greater than the second frequency.

12 Claims, 8 Drawing Sheets

DENTAL TOOL DISPLACEMENT APPARATUS WITH SLOW ROTATIONAL MOTION

The application claims the benefit to Provisional Patent Application No. 61/219,812 filed Jun. 24, 2009.

FIELD AND BACKGROUND OF THE INVENTION

The present invention relates to equipment used in dental applications and, in particular, a handpiece or handpiece accessory for use in endodontic and other dental applications to provide a slow secondary rotary motion to enhance uniformity of results when using a rapidly oscillating tool.

Historically, endodontic devices have been proposed which employ a wide range of up-down oscillating motion, rotary motion and various compound motions. Where more than one mode of motion is provided, the frequency of the different modes of motion are typically similar. For devices operating with a rotary motion, speeds of rotation are typically in excess of about 200 rpm, and in many cases, thousands of rpm.

The present invention relates particularly to a subclass of tools for which the primary motion is a longitudinal reciprocating motion, i.e., along a line corresponding to the length of the tool. One non-limiting but particularly preferred example is the self-adjusting file described in European Patent No. EP 1708638 B1, which is hereby incorporated by reference in its entirety.

During operation of a tool with purely longitudinal reciprocating motion, there is a risk that uneven wear may occur to the tool and/or that a tool that is not rotationally symmetric may result in non-uniform results in the tissue being treated. Certain commercially available handpieces which provide reciprocating motion allow for free rotation of the tool during use, thought to reduce stress in the tool. However, this freedom of rotation does not ensure that rotation will occur during use.

There is therefore a need for a dental tool displacement apparatus handpiece, or an accessory for use with an existing handpiece, which would provide slow rotation of a tool while the tool undergoes relatively higher frequency reciprocating motion, thereby enhancing the uniformity of operation of the tool. It would also be particularly advantageous to provide a compact and effective transmission arrangement which would allow both reciprocating and rotational motions in any desired ratio to be derived from a single drive motor.

SUMMARY OF THE INVENTION

The present invention is a dental tool displacement apparatus and corresponding method.

According to the teachings of the present invention there is provided, a dental tool displacement apparatus for use with a motorized power handle to displace a dental tool, the displacement apparatus comprising: (a) a tool holder having a receptacle for receiving the dental tool, the receptacle defining a tool axis; (b) a drive arrangement associated with the tool holder and the motorized power handle, the drive arrangement defining a transmission from the motorized power handle to the tool holder such that the tool holder undergoes reciprocating motion parallel to the tool axis at a first frequency of oscillations per minute and rotates about the tool axis at a second frequency of rotations per minute, wherein the first frequency is at least one order of magnitude greater than the second frequency.

According to a further feature of the present invention, the drive arrangement defines a transmission from the motorized power handle to the tool holder such that, for each reciprocating motion of the tool holder parallel to the tool axis, the tool holder rotates through a rotational step of no more than a fortieth of a revolution about the tool axis.

According to a further feature of the present invention, the first frequency is at least two orders of magnitude greater than the second frequency.

According to a further feature of the present invention, the drive arrangement defines a transmission from the motorized power handle to the tool holder such that, when the tool holder experiences torque greater than a threshold value opposing the rotation about the tool axis, the rotation is interrupted while the reciprocating motion is substantially unaffected.

According to a further feature of the present invention, for use with a motorized power handle having a drive pin eccentrically mounted on an output drive shaft, the drive arrangement comprises an annular slot circumscribing the tool axis, the annular slot being formed between a first and a second opposing surfaces, the annular slot receiving the eccentrically mounted drive pin so that motion of the drive pin within the annular slot generates the reciprocating motion of the tool holder, and wherein the first opposing surface is provided with a sequence of axially projecting gear teeth arrayed around the axis such that, during a revolution of the output shaft, the drive pin engages the gear teeth, generates a rotational step of the first opposing surface and disengages from the gear teeth.

According to a further feature of the present invention, the first opposing surface is mechanically integrated with the tool holder.

According to a further feature of the present invention, the drive arrangement further comprises a supplementary transmission stage interconnecting between the first opposing surface and the tool holder such that a given rotational step of the first opposing surface generates a different rotational step of the tool holder.

According to a further feature of the present invention, the supplementary transmission stage comprises a planetary gear arrangement centered on the tool axis.

There is also provided according to the teachings of the present invention, a dental tool hand piece comprising: (a) the dental tool displacement apparatus as described above; and (b) a motorized power handle, the dental tool displacement apparatus being engaged with the motorized power handle so as to be driven by the motorized power handle.

There is also provided according to the teachings of the present invention, a method for operating a dental tool, the method comprising the steps of: (a) providing a dental tool having a tool axis and configured for operating by axial oscillatory motion; (b) deploying the dental tool in juxtaposition with dental tissue; (c) generating axial oscillatory motion at a first frequency of oscillations per minute; and (d) during the axial oscillatory motion, generating rotation about the tool axis at a second frequency of rotations per minute, wherein the first frequency is at least one order of magnitude greater than the second frequency.

There is also provided according to the teachings of the present invention, a dental tool displacement apparatus for use with a motorized power handle having a drive pin eccentrically mounted on an output drive shaft to displace a dental tool, the displacement apparatus comprising: (a) a tool holder having a receptacle for receiving the dental tool, the receptacle defining a tool axis; (b) a drive arrangement associated with the tool holder and the motorized power handle, the drive arrangement comprising an annular slot circumscribing the tool axis, the annular slot being formed between first and second opposing surfaces, the annular slot receiving the eccentrically mounted drive pin so that motion of the drive pin within the annular slot generates reciprocating motion of the tool holder parallel to the tool axis at a first frequency of oscillations per minute, and wherein the first opposing surface is provided with a sequence of axially projecting gear teeth such that, during a revolution of the output shaft, the drive pin engages the gear teeth, generates a rotational step of the first opposing surface, and disengages from the gear teeth, thereby generating rotation of the tool holder about the tool axis at a second frequency of rotations per minute.

According to a further feature of the present invention, the first opposing surface is mechanically integrated with the tool holder.

According to a further feature of the present invention, the drive arrangement further comprises a supplementary transmission stage interconnecting between the first opposing surface and the tool holder such that a given rotational step of the first opposing surface generates a different rotational step of the tool holder.

According to a further feature of the present invention, the supplementary transmission stage comprises a planetary gear arrangement centered on the tool axis.

BRIEF DESCRIPTION OF THE DRAWINGS

The invention is herein described, by way of example only, with reference to the accompanying drawings, wherein:

FIGS. 5A-5E are a sequence of schematic views illustrating the operation of part of a drive arrangement from the dental tool displacement apparatus of FIG. 2;

DESCRIPTION OF THE PREFERRED EMBODIMENTS

The present invention is a dental tool displacement apparatus and method.

The principles and operation of a dental tool displacement apparatus and method according to the present invention may be better understood with reference to the drawings and the accompanying description.

Figure 1:
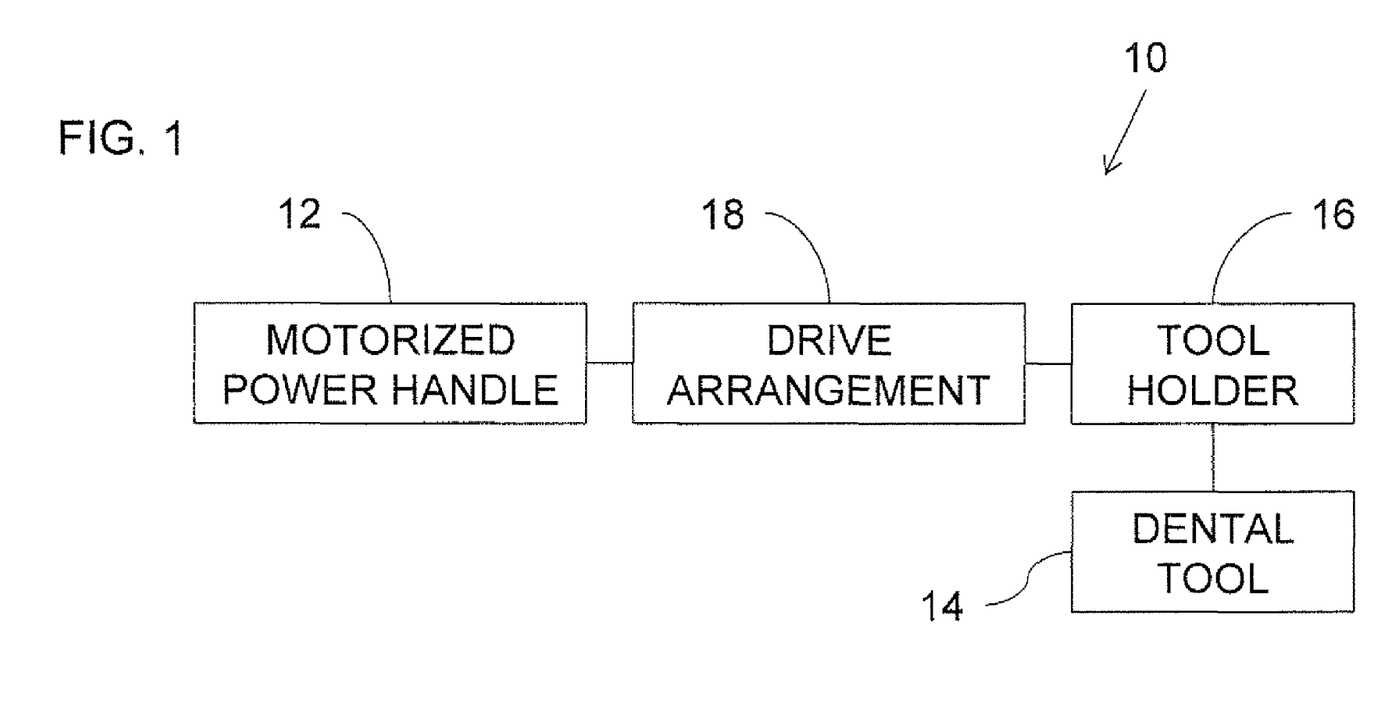
FIG. 1 is a schematic block diagram of a dental tool displacement apparatus, constructed and operative according to the teachings of the present invention.

Referring now to the drawings, FIG. 1 illustrates schematically a dental tool displacement apparatus, generally designated 10, constructed and operative according to the teachings of the present invention, for use with a motorized power handle 12 to displace a dental tool 14. Generally speaking, displacement apparatus 10 includes a tool holder 16 having a receptacle for receiving dental tool 14, and a drive arrangement 18, associated with tool holder 16 and motorized power handle 12. Drive arrangement 18 defines a transmission from motorized power handle 12 to tool holder 16 such that tool holder 16 undergoes reciprocating motion parallel to the tool axis at a first frequency of oscillations per minute and rotates about the tool axis at a second frequency of rotations per minute. According to an embodiment of the present invention, the first frequency is at least one order of magnitude greater than the second frequency.

At this stage, it will already be apparent that an embodiment of the present invention provides a highly advantageous displacement apparatus in which uniformity of operation of a reciprocating tool is ensured by superimposing a slower rotary motion on the primary reciprocating motion. As a result, any unevenness of action of the tool around its circumference is averaged out during the rotation. This and other advantages of certain embodiments of the present invention will become clearer from the subsequent examples.

At this point, it will be helpful to define certain terminology as used herein in the description and claims. Firstly, reference is made to a "motorized power handle 12." This refers to a handle, to be held by the user while operating the dental tool, from which motive power is supplied to move the tool. The motion may be generated by a motor located within the handle, driven for example by electricity or compressed air, or may be provided via a mechanical linkage from a remote motor. The motorized power handle may be a standard off-the-shelf item, such as is commercially available in handpieces for driving reciprocating tools, or may be a dedicated device, optionally integrated with other parts of the dental tool displacement apparatus.

The term "receptacle" is used herein to refer to any structure for engaging a tool. In many cases, the receptacle is a socket which receives a shank of the dental tool, but all other structures suitable for defining effective mechanical engagement between a dental tool and its tool holder also falls within the scope of the term "receptacle".

The term "dental tool" is used herein to refer generically to substantially any tool used in dental applications. Of particular relevance to certain embodiments of the present invention are endodontic tools such as are used for preparation of a root canal.

The tool itself, or the manner in which it is held in a tool holder, is taken to define a "tool axis" along which the primary reciprocating motion takes place. In the case of a flexible tool, where different parts of the tool may extend in different directions, the "tool axis" is defined as the central axis of the shank of the tool.

The term "mechanically integrated" refers to components which are rigidly attached or integrally formed so as to move together as a single body.

The term "frequency" is used to refer to the average frequency of a cyclic motion, defined by a total number of cycles occurring per minute. This terminology is used to refer to the overall motion, independent of whether the motion is implemented as smooth continuous motion or a sequence of small discrete steps.

Figure 4A:
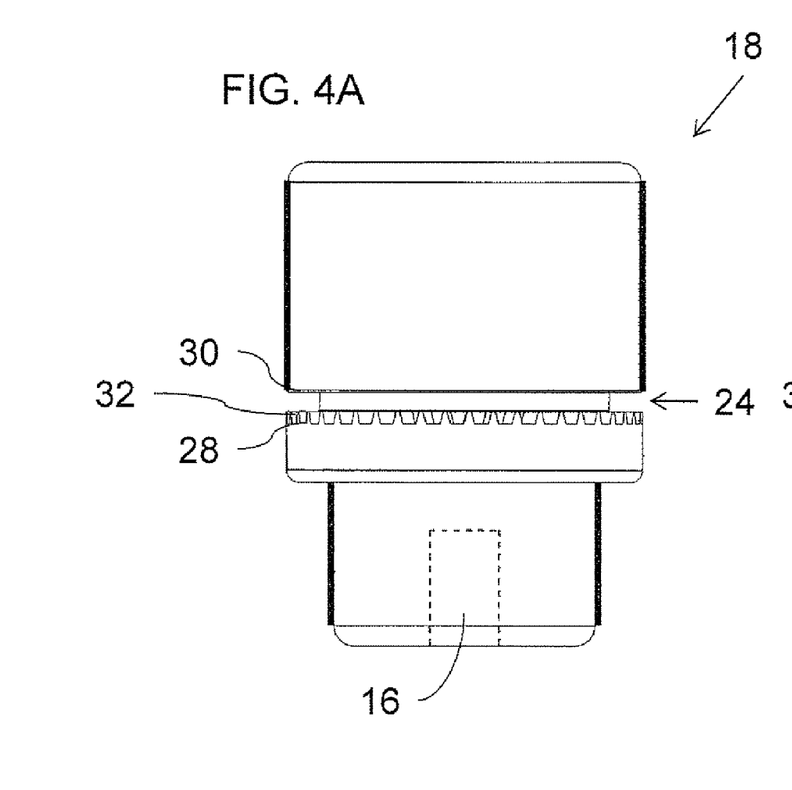
FIGS. 4A and 4B are side views of a part of a drive arrangement according to two alternative implementations of the dental tool displacement apparatus of FIG. 2.
Figure 4B:
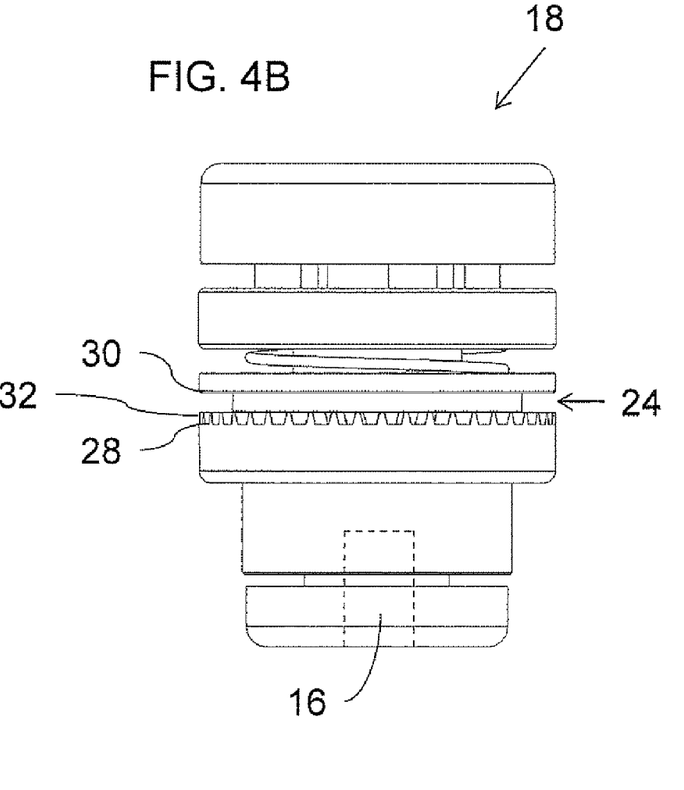
Figure 5A:
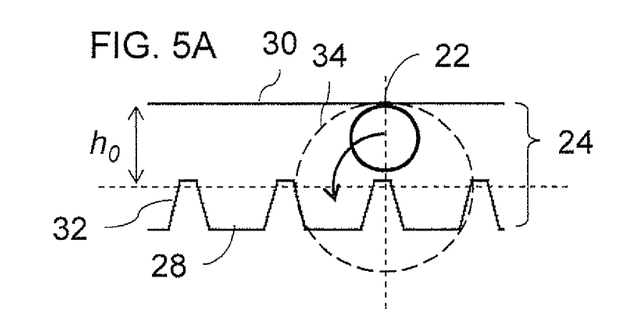
Figure 5B:
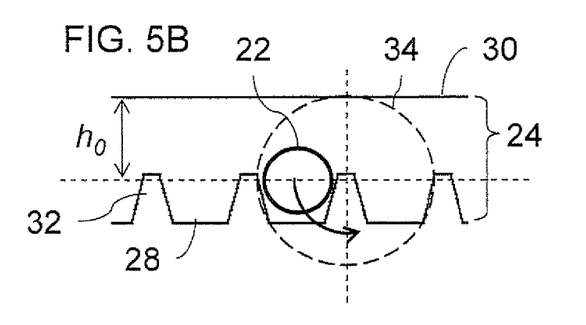
Figures 5C, 5D, 5E:
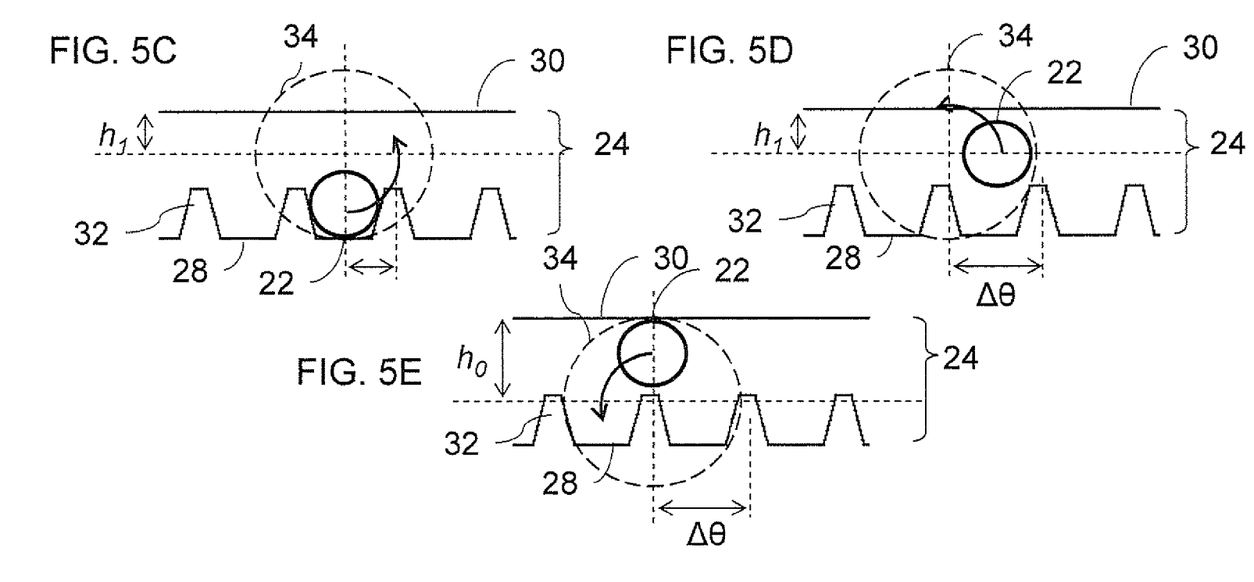
Figure 6:
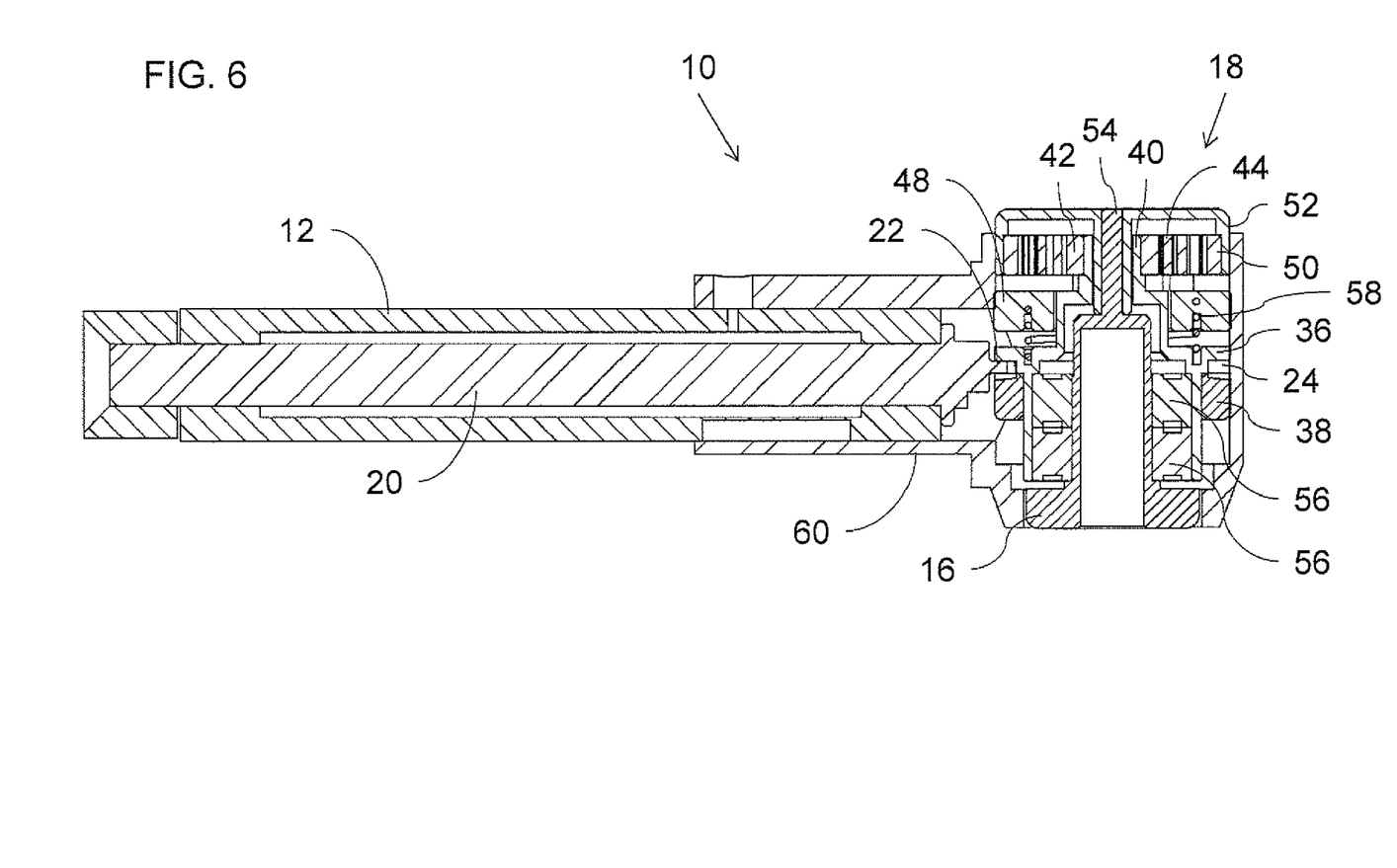
FIG. 6 is a longitudinal cross-sectional view taken through the dental tool displacement apparatus of FIG. 2.

Turning now to FIGS. 2-8, there is shown an exemplary implementation of the device of FIG. 1. As best seen in FIG. 6, displacement apparatus 10 is here illustrated in a non-limiting example of a device operating with a motorized power handle 12 which provides motion through a rotating drive shaft 20 which terminates in an eccentrically-mounted drive pin 22. Rotation of drive shaft 20 displaces pin 22 in a circular motion.

Figure 2:
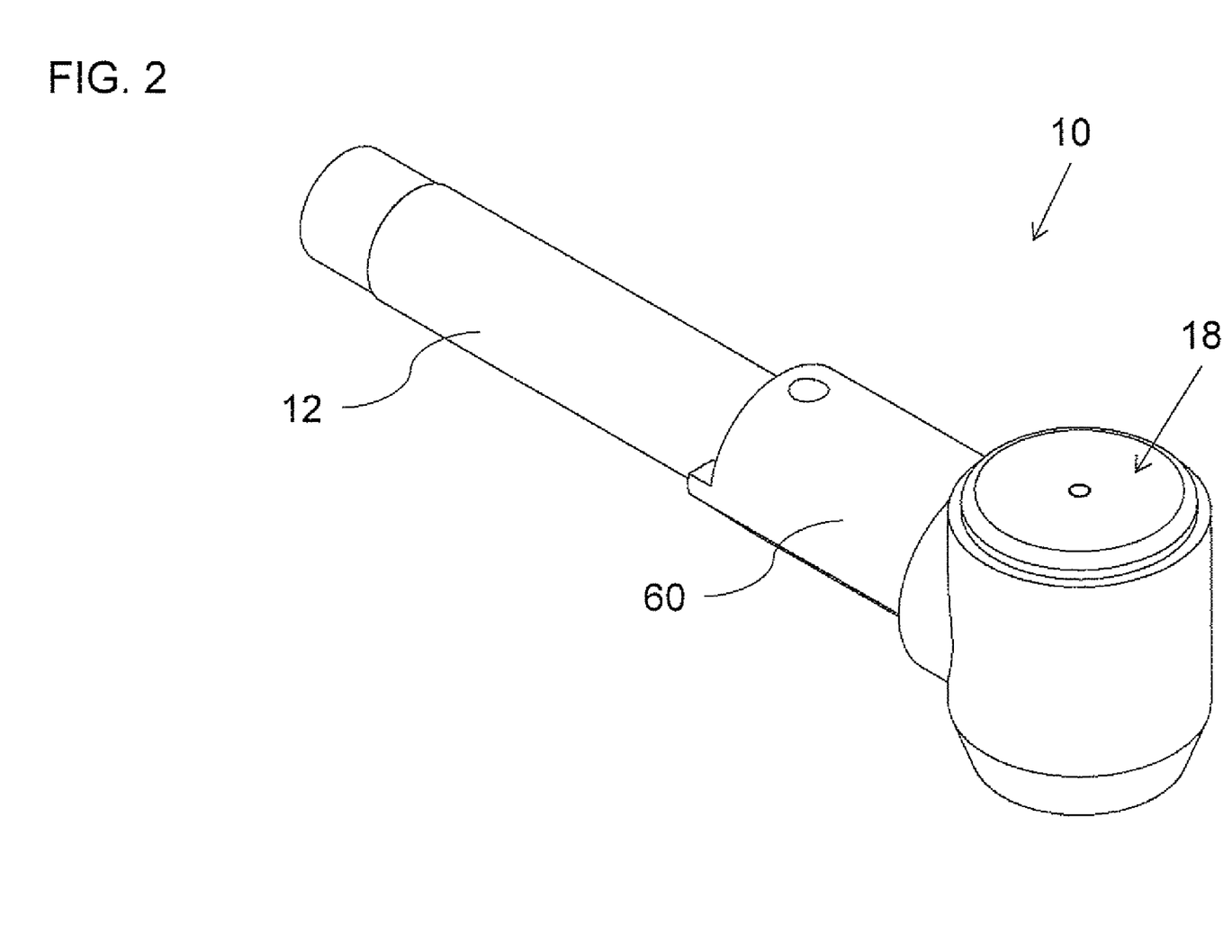
FIG. 2 is an isometric view of an exemplary implementation of the dental tool displacement apparatus of FIG. 1.
Figure 3:
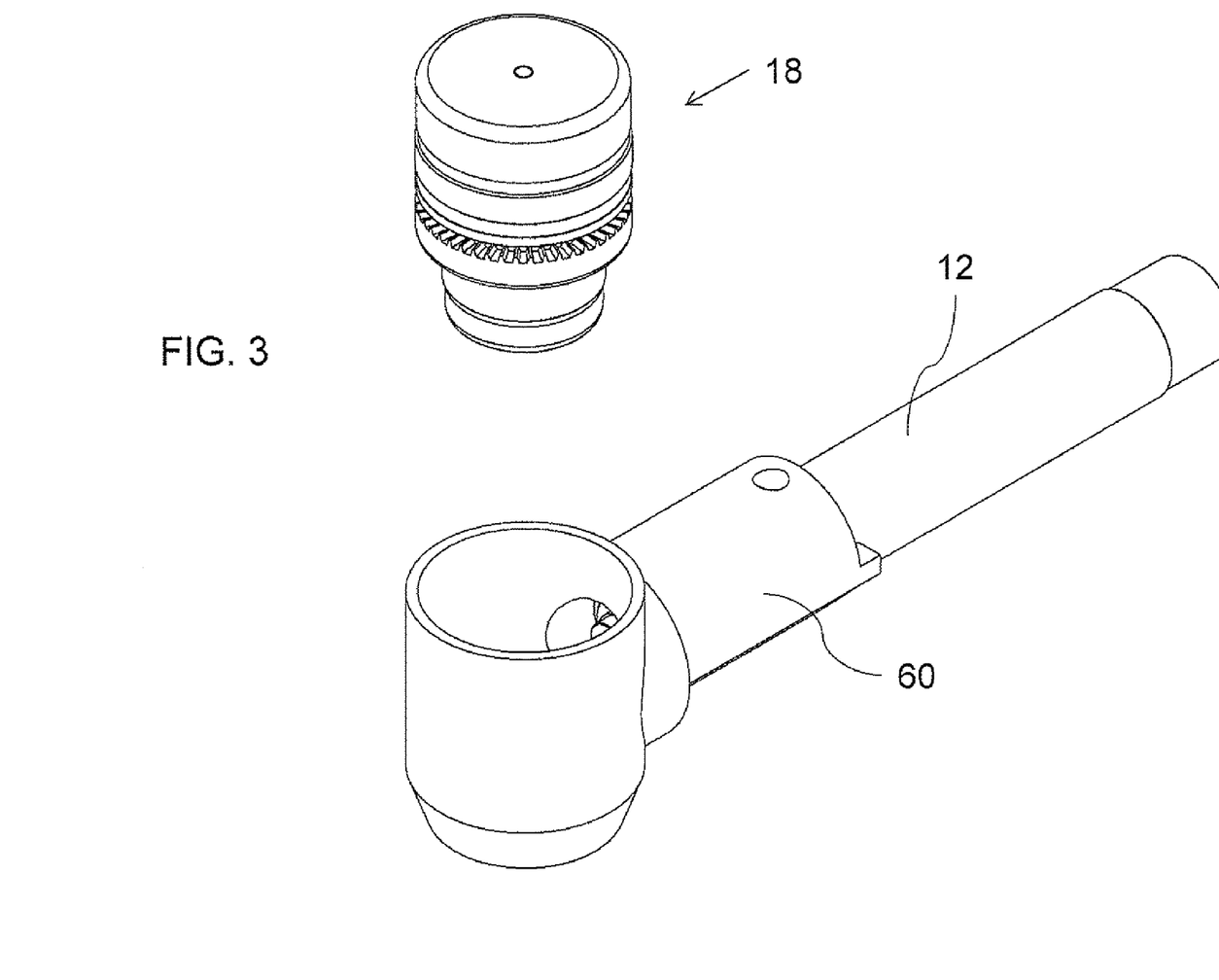
FIG. 3 is a partially disassembled isometric view of the dental tool displacement apparatus of FIG. 2.

Drive arrangement 18, in both of the two variant examples of FIGS. 4A and 4B, includes an annular slot 24 circumscribing the tool axis 26 within which eccentrically mounted drive pin 22 is received. The engagement of drive pin 22 within slot 24 converts the circular motion of pin 22 into the aforementioned axial reciprocating motion of tool holder 16. Drive arrangement 18 is held in a predefined relation to motorized power handle 12 by an outer housing 60, configured to allow the required reciprocating and rotary motion of drive arrangement 18, as seen in FIGS. 2, 3 and 6.

Slot 24 is delimited by first and second opposing surfaces 28 and 30. In the implementation shown here, first opposing surface 28 is provided with a sequence of axially projecting gear teeth 32 around its circumference. As a result, during a revolution of drive shaft 20, drive pin 22 engages the gear teeth 32, generates a rotational step of surface 28 around tool axis, and disengages from the gear teeth 32. It should be noted that gear teeth 32 are referred to as "projecting axially" in the sense that they lie above the level of the underlying surface 28, thereby distinguishing them from radial spur gear teeth, but without implying any specific axial features or geometry.

The interaction of drive pin 22 within slot 24 and the resulting motion of surfaces 28 and 30 are schematically represented in FIGS. 5A-5E. To facilitate understanding of the motion, a dashed circle 34 is used to designate the circle of motion of drive pin 22 and dashed cross-hairs are shown passing through the center of that circle, corresponding to the axis of rotation of drive shaft 20 of the motorized power handle.

FIG. 5A shows an arbitrarily selected initial position of drive pin 22 at its highest position, abutting surface 30. In this state, the axial distance between the horizontal cross-hair and surface 30 is a maximum, denoted $h_0$. As drive shaft 20 continues to rotate, drive pin 22 moves successively to the positions shown in FIGS. 5B and 5C, engaging gear teeth 32. This motion presses downwards on surface 28, thereby displacing the assembly downwards until it reaches its lowest point as shown in FIG. 5C, with the axial distance between the horizontal cross-hair and surface 30 denoted $h_1$. The horizontal component of the motion of drive pin 22 engaged with teeth 32 also causes angular displacement of surface 28 about axis 26, reaching an angular step $\Delta\theta$ as drive pin 22 clears the teeth 32 (FIG. 5D). As drive pin 22 completes its rotation cycle, returning to its highest position as shown in FIG. 5E, it bears upwards on surface 30, thereby displacing the assembly upwards to restore the vertical position to $h_0$ above the horizontal cross-hair. In the horizontal direction, drive pin 22 slides against smooth surface 30, leaving the net rotational step of $\Delta\theta$ from the cycle, which then repeats.

Thus the overall effect of each revolution of drive shaft 20 is normally one cycle of axial reciprocating motion with an amplitude $(h_0-h_1)$ and a rotation step of $\Delta\theta$ about axis 26. The size of the rotation step may be varied, but is determined primarily by the size of the eccentric offset of drive pin 22 as well as the diameter of surface 28. In certain preferred embodiments, $\Delta\theta$ is no more than a fortieth of a revolution, corresponding to at least forty teeth 32 disposed around surface 28.

Another valuable feature of certain embodiments of the present invention exemplified by this assembly is the interruption of rotation when significant resistance is encountered. Specifically, it will be noted that drive pin 22 is disengaged from teeth 32 during a significant part of each cycle (see FIGS. 5D and 5E). In the event that the tool encounters torque greater than a certain threshold value opposing rotation, the assembly will tend to recoil as drive pin 22 disengages teeth 32, thereby reducing or canceling the rotation step $\Delta\theta$ of the preceding cycle and avoiding application of possibly damaging high rotational torques through the dental tool. At the same time, the primary axial reciprocating motion continues, thereby allowing continued operation with the tool.

In certain embodiments, the aforementioned motion generated by the interaction of drive pin 22 with slot 24 is appropriate. In such cases, first opposing surface 28 is preferably mechanically integrated with tool holder 16, as illustrated schematically in the implementation of FIG. 4A. In this case, the overall motion of the tool holder (and tool, not shown) during use will be the same as that described above with reference to FIGS. 5A-5E, namely, axial reciprocating motion at a first frequency combined with rotation about the axis at a lower frequency, typically corresponding to one revolution for every 40-50 cycles of reciprocating motion.

In certain embodiments it may be desirable to obtain an overall ratio between frequencies of the axial oscillation and the rotation outside the range of what can be achieved directly by the aforementioned approach. In such cases, drive arrangement 18 preferably also includes a second step-down (or step-up) transmission stage interconnecting between the first opposing surface and the tool holder such that a given rotational step of the first opposing surface generates a different rotational step of the tool holder. An example of such an embodiment will now be described with reference to FIGS. 4B and 6-8.

Figure 7:
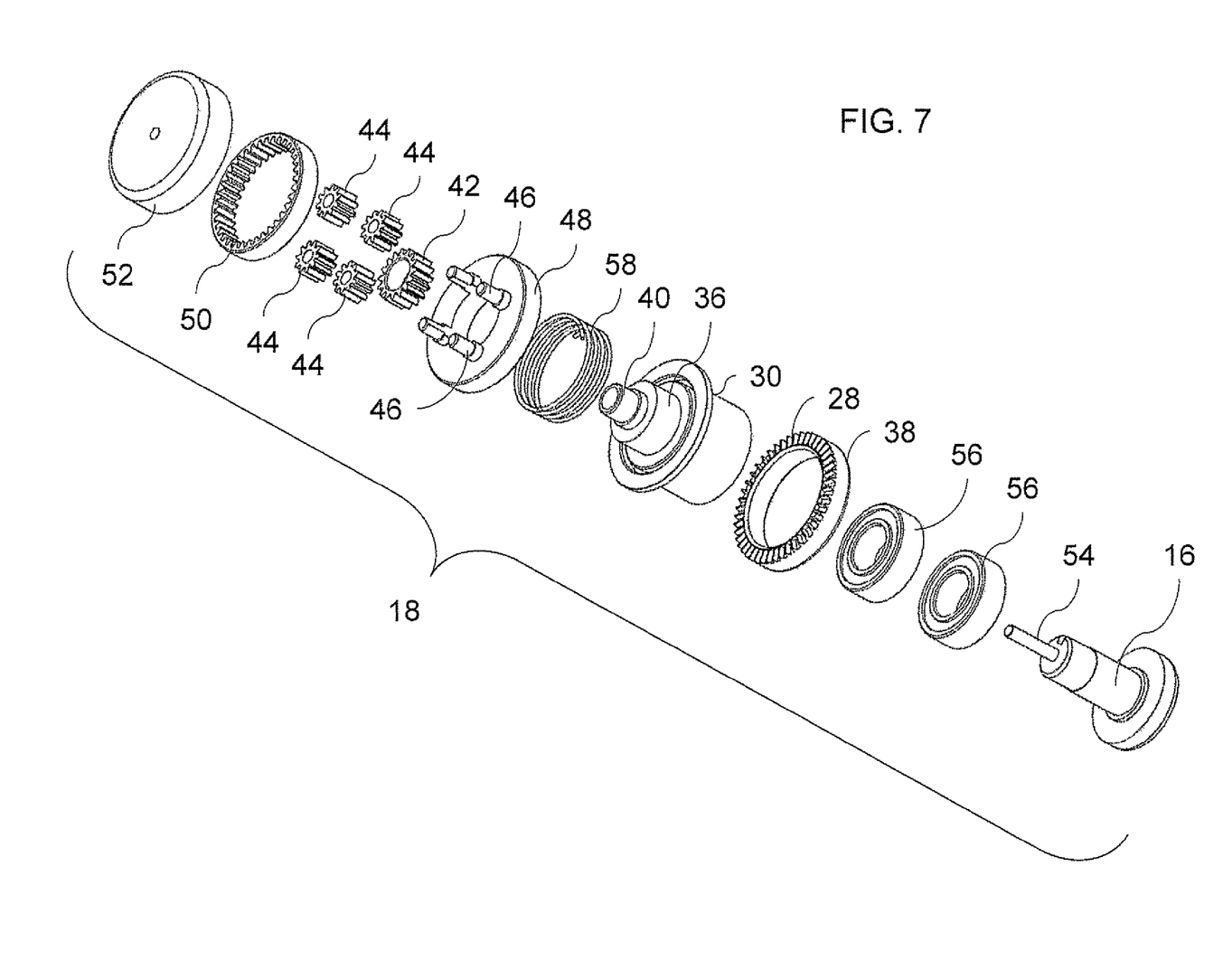
FIG. 7 is an exploded isometric view of the part of the drive arrangement shown in FIG. 4B.
Figure 8:
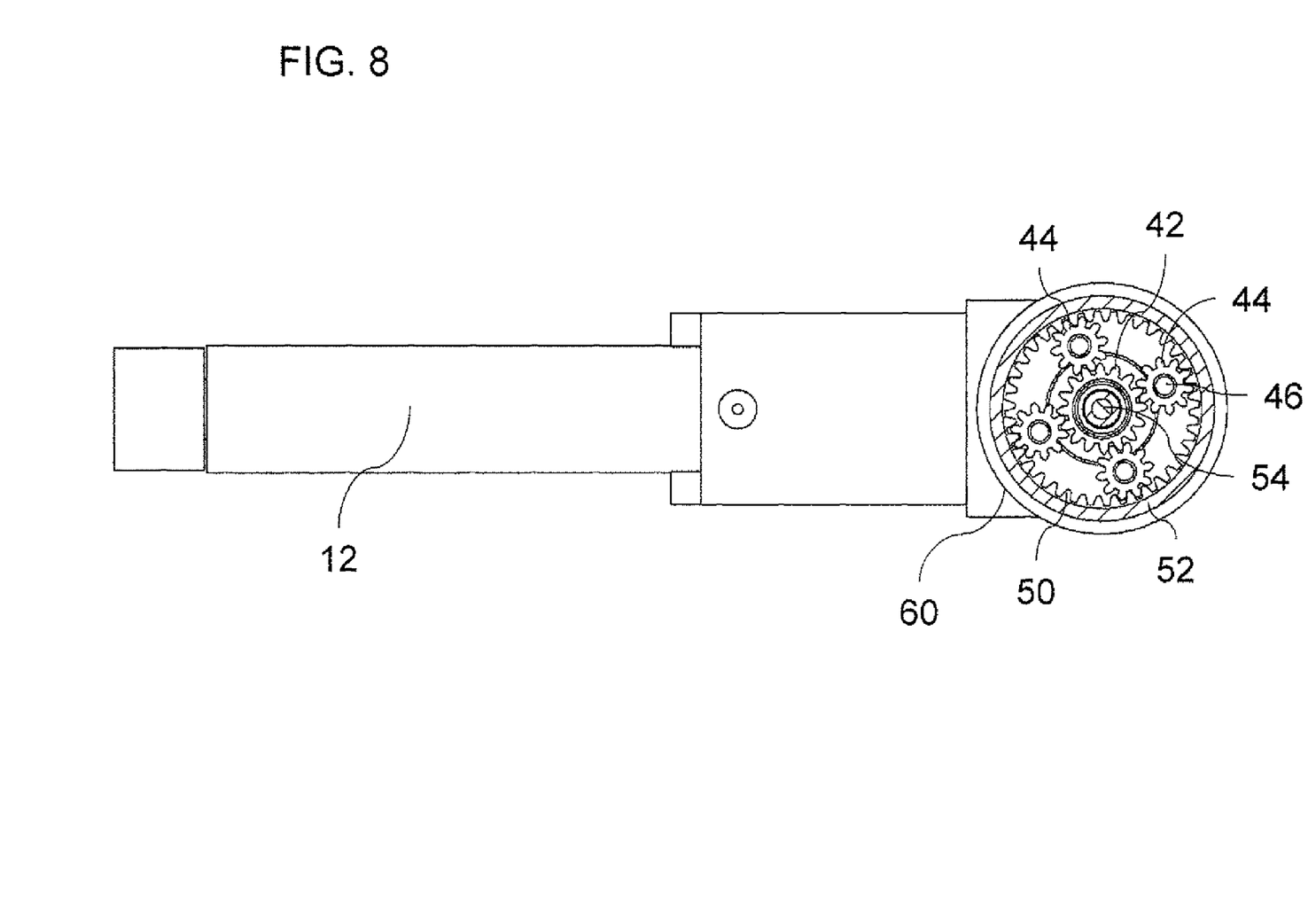
FIG. 8 is a top view of the dental tool displacement apparatus of FIG. 2 with a cover element removed to reveal a planetary gear step-down arrangement according to an implementation of the dental tool displacement apparatus of FIG. 2.

The structure and function of drive mechanism 18 of FIG. 4B will be best understood by referring in parallel to FIGS. 6 and 7, where the exploded view of FIG. 7 shows clearly the structure of each component while the sectional view of FIG. 6 shows the interrelation between the components when assembled. Slot 24 is defined by surface 30 provided by a hollow rotating body 36 and opposing surface 28 which is provided by a gear ring 38 which is mechanically integrated therewith, for example, by press fitting. Rotating body 36 terminates at its upper end in a hollow shaft 40 to which is attached a sun gear 42 which forms the center of a planetary gear arrangement. At least two, and preferably three or more, planet gears 44 are rotatably mounted on posts 46 of a fixed support block 48, which is preferably fixed relative to the housing of motorized power handle 12. An outer ring gear 50 engages planet gears 44. The overall deployment of the planetary gear arrangement is best seen in FIG. 8. A connecting cover 52 is mechanically integrated with outer ring gear 50 and with an axial stem 54 projecting upwards from tool holder 16 through hollow shaft 40. One or more bearing collar 56 are interposed between tool holder 16 and rotating body 36 so as to maintain concentric alignment of the components while allowing low-friction relative rotation of tool holder 16 and rotating body 36. In the implementation illustrated here, a compression spring 58 applies a bias force between support block 48 and rotating body 36 in order to bias the tool holder to its lowered position when not in motion, and to maintain a well defined frictional contact between the various moving components.

In operation, drive shaft 20 conveys rotational motion to rotating body 36 by motion of drive pin 22 within slot 24 as described above with reference to FIGS. 5A-5E. Sun gear 42 rotates together with rotating body 36, causing rotation of planet gears 44 about their fixed axes (posts 46). This in turn causes outer ring gear 50 to turn, thereby also turning connecting cover 52 and tool holder 16. The overall result is that tool holder 16 moves in angular steps, and at a frequency, related to those of rotating body 36 by the ratio of the number of teeth between sun gear 42 and outer ring gear 50. In the case illustrated here, the secondary transmission provided by the planetary gear arrangement provides an addition step-down ratio of about 4:1. This allows implementation of a drive arrangement 18 with an overall difference of at least two orders of magnitude between the frequency of reciprocating motion and that of rotation.

By way of example, certain embodiments of the present invention are intended primarily for use with dental tools referred to as "low speed", often defined as operating speeds less than 20,000 oscillations per minute (opm). Typically, certain embodiments operate with reciprocating motion in excess of 2,000 opm, and most preferably in the range of 3,000-5,000 opm. In the context of this preferred range of 3,000-5,000 opm, the single stage implementation of FIG. 4A preferably results in a rotary motion at a frequency between about 60 and about 120 rpm, while a two stage implementation as exemplified in FIG. 4B preferably reduces the rotary motion frequency to less than 40 rpm, and typically in the range of 10-30 rpm.

As mentioned earlier, certain embodiments of the present invention are of particular value when used with endodontic files, and particularly with files operating primarily with an axial reciprocating movement, but which have an open structure (for example, at least 50% open), or which is otherwise significantly asymmetric under rotation about the axis. In such cases, addition of a rotational motion about the axis helps to ensure uniform operation of the tool. A particularly preferred example of a tool for use in combination with certain embodiments of the present invention is the self-adjusting file of the aforementioned European Patent No. EP 1708638 B1.

Parenthetically, with regard to the secondary transmission, although described herein in the context of certain exemplary embodiments with increased step-down ratios, it will be noted that the planetary gear arrangement can readily be rearranged to provide a step-up gear ratio, thereby for example reducing the overall ratio between the reciprocation frequency and the rotation frequency down to significantly less than the 40-50 ratio native to the drive pin transmission arrangement, and in some cases, to an overall ratio less than 10:1. The particular desired output ratio will be determined according to the considerations for each given application based on the structural principles described herein, as will be clear to one ordinarily skilled in the art.

Although particular embodiments of the present invention have been described to illustrate a wide range of features, it should be noted that the invention is not limited to these specific implementations. For example, it should be noted that a similar effect may be obtained in some cases by providing surfaces 28 and 30 on opposing sides of slot 24 with materials and/or surface characteristics which provide one surface of relatively high friction and one of relatively low friction, thereby achieving horizontal displacement as pin 22 moves in contact with one surface but not with the other. Furthermore, the invention is not limited to use with motorized drive handles with an eccentric drive pin as the output interface, and may equally be implemented where part or all of the motive power is provided by some other form of interface, such as by a rotating gear wheel.

It will be appreciated that the above descriptions are intended only to serve as examples, and that many other embodiments are possible within the scope of the present invention as defined in the appended claims.

What is claimed is:

1. A dental tool displacement apparatus for use with a motorized power handle having a drive pin eccentrically mounted on an output drive shaft to displace a dental tool, the displacement apparatus comprising:
   (a) a tool holder having a receptacle for receiving the dental tool, said receptacle defining a tool axis;
   (b) a drive arrangement associated with said tool holder and the motorized power handle, said drive arrangement defining a transmission from the motorized power handle to said tool holder such that said tool holder undergoes reciprocating motion parallel to said tool axis at a first frequency of oscillations per minute and rotates about said tool axis at a second frequency of rotations per minute,
   wherein said first frequency is at least one order of magnitude greater than said second frequency,
   and wherein said drive arrangement comprises an annular slot circumscribing said tool axis, said annular slot being formed between a first and a second opposing surfaces, said annular slot receiving the eccentrically mounted drive pin so that motion of the drive pin within said annular slot generates said reciprocating motion of said tool holder, and wherein said first opposing surface is provided with a sequence of axially projecting gear teeth arrayed around said axis such that, during a revolution of the output shaft, the drive pin engages said gear teeth, generates a rotational step of said first opposing surface and disengages from said gear teeth.

2. The displacement apparatus of claim 1, wherein said drive arrangement defines a transmission from the motorized power handle to said tool holder such that, for each reciprocating motion of said tool holder parallel to said tool axis, said tool holder rotates through a rotational step of no more than a fortieth of a revolution about said tool axis.

3. The displacement apparatus of claim 1, wherein said first frequency is at least two orders of magnitude greater than said second frequency.

4. The displacement apparatus of claim 1, wherein said drive arrangement defines a transmission from the motorized power handle to said tool holder such that, when said tool holder experiences torque greater than a threshold value opposing said rotation about said tool axis, said rotation is interrupted while said reciprocating motion is substantially unaffected.

5. The displacement apparatus of claim 1, wherein said first opposing surface is mechanically integrated with said tool holder.

6. The displacement apparatus of claim 1, wherein said drive arrangement further comprises a supplementary transmission stage interconnecting between said first opposing surface and said tool holder such that a given rotational step of said first opposing surface generates a different rotational step of said tool holder.

7. The displacement apparatus of claim 6, wherein said supplementary transmission stage comprises a planetary gear arrangement centered on said tool axis.

8. A dental tool hand piece comprising:
   (a) the dental tool displacement apparatus of claim 1; and
   (b) a motorized power handle, said dental tool displacement apparatus being engaged with said motorized power handle so as to be driven by said motorized power handle.

9. A dental tool displacement apparatus for use with a motorized power handle having a drive pin eccentrically mounted on an output drive shaft to displace a dental tool, the displacement apparatus comprising:
   (a) a tool holder having a receptacle for receiving the dental tool, said receptacle defining a tool axis;
   (b) a drive arrangement associated with said tool holder and the motorized power handle, said drive arrangement comprising an annular slot circumscribing said tool axis, said annular slot being formed between first and second opposing surfaces, said annular slot receiving the eccentrically mounted drive pin so that motion of the drive pin within said annular slot generates reciprocating motion of said tool holder parallel to said tool axis at a first frequency of oscillations per minute, and wherein said first opposing surface is provided with a sequence of axially projecting gear teeth such that, during a revolution of the output shaft, the drive pin engages said gear teeth, generates a rotational step of said first opposing surface, and disengages from said gear teeth, thereby generating rotation of said tool holder about said tool axis at a second frequency of rotations per minute.

10. The displacement apparatus of claim 9, wherein said first opposing surface is mechanically integrated with said tool holder.

11. The displacement apparatus of claim 9, wherein said drive arrangement further comprises a supplementary transmission stage interconnecting between said first opposing surface and said tool holder such that a given rotational step of said first opposing surface generates a different rotational step of said tool holder.

12. The displacement apparatus of claim 11, wherein said supplementary transmission stage comprises a planetary gear arrangement centered on said tool axis.

* * * * *